(12) United States Patent
Alter et al.

(10) Patent No.: US 10,289,640 B2
(45) Date of Patent: May 14, 2019

(54) METHOD AND SYSTEM FOR RETRIEVAL OF FINDINGS FROM REPORT DOCUMENTS

(71) Applicant: OPISOFTCARE LTD., Tel-Aviv (IL)

(72) Inventors: Alon Alter, Raanana (IL); Oksana Tozhovez, Petah-Tiqwa (IL)

(73) Assignee: OPISOFTCARE LTD., Tel-Aviv (IL)

( * ) Notice: Subject to any disclaimer, the term of this patent is extended or adjusted under 35 U.S.C. 154(b) by 269 days.

(21) Appl. No.: 15/502,101

(22) PCT Filed: Aug. 10, 2015

(86) PCT No.: PCT/IL2015/000038
§ 371 (c)(1),
(2) Date: Feb. 6, 2017

(87) PCT Pub. No.: WO2016/024262
PCT Pub. Date: Feb. 18, 2016

(65) Prior Publication Data
US 2017/0228455 A1 Aug. 10, 2017

Related U.S. Application Data

(60) Provisional application No. 62/037,697, filed on Aug. 15, 2014.

(51) Int. Cl.
| | | |
|---|---|---|
| G06F 17/30 | (2006.01) | |
| G06F 16/33 | (2019.01) | |
| G16H 50/70 | (2018.01) | |
| G06F 16/35 | (2019.01) | |
| G06F 16/248 | (2019.01) | |
| G06F 16/2457 | (2019.01) | |
| G06F 19/00 | (2018.01) | |

(52) U.S. Cl.
CPC ......... *G06F 16/334* (2019.01); *G06F 16/248* (2019.01); *G06F 16/2457* (2019.01); *G06F 16/35* (2019.01); *G06F 17/30522* (2013.01); *G06F 17/30554* (2013.01); *G06F 17/30675* (2013.01); *G06F 17/30705* (2013.01); *G06F 19/00* (2013.01); *G06F 19/324* (2013.01); *G16H 50/70* (2018.01)

(58) Field of Classification Search
CPC ......... G06F 17/30522; G06F 17/30554; G06F 17/30675; G06F 17/30705
See application file for complete search history.

*Primary Examiner* — Joshua Bullock
(74) *Attorney, Agent, or Firm* — The Law Office of Michael E. Kondoudis

(57) ABSTRACT

System and method used to provide fast and accurate retrieval of findings results from large amounts of report documents (the corpus), such as medical record documents. The system maintains a dynamic list of the characteristics of no-finding called no-finding descriptors, each identified by a tag. Upon entering the corpus, the sentences of each new document are searched, and each sentence the content of which is similar to one of the descriptors is tagged. When search is conducted, the user enters a word or phrase, which expresses the subject of search. This subject is searched for in the corpus and from which a list of all sentences that contain the subject—the initial result list. This initial results list includes both finding and no-finding results. The final result list is obtained by extracting from the initial result list all occurrences of the tagged no-finding sentences.

8 Claims, 4 Drawing Sheets

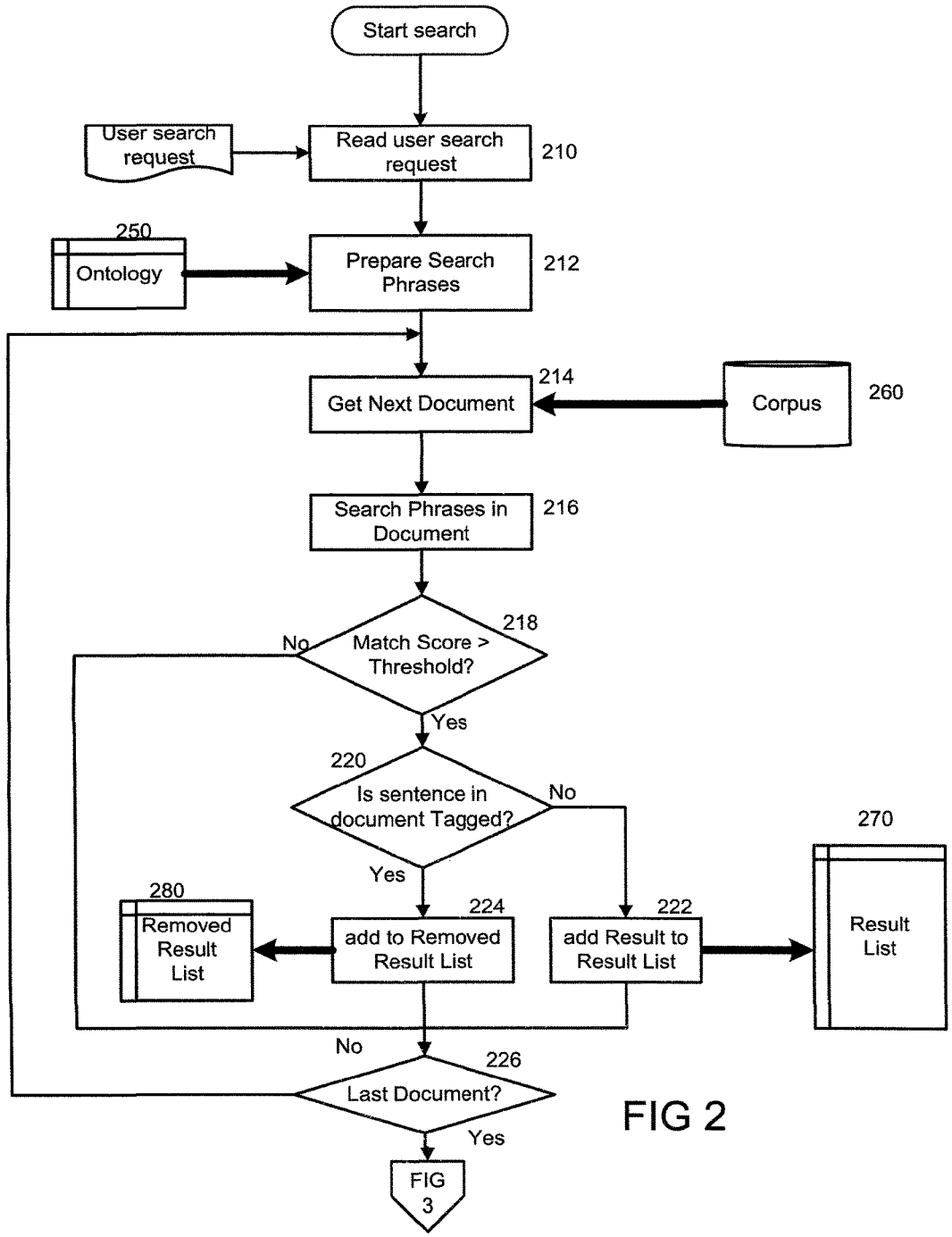

METHOD AND SYSTEM FOR RETRIEVAL OF FINDINGS FROM REPORT DOCUMENTS

FIELD OF THE INVENTION

The invention generally relates to the field of information retrieval and more particularly to retrieving information by eliminating its complement.

BACKGROUND OF THE INVENTION

The computerization of medical records and medical services has opened the door to many IT innovations. This is true particularly in the areas of advanced and accurate text search engines. The importance of accurate results to a doctor and researches searching through medical documents like pathology and radiology reports, admission and discharge documents, nurses notes etc. . . . ) is paramount. As such, it is important to perform the search not only for the right results (say you are looking for lungs disease), it is also important to leave out of the search results documents that show "no pathological findings" in the lungs.

Current search engines find all documents containing specific words or phrases. These searches have high false positive results, i.e. they retrieve many documents that does not contain the required information. The search can also miss important data. The reason is that the search query does not cover all possible expressions of the requested data. However, medical searches require high reliability.

US patent application 2012/0179696 by Charlot et all "System and process for concept tagging and concept retrieval" discloses a system and process for tagging documents in order to facilitate later retrieval. The tagged concepts are well-defined clinical finding. Hence, well-defined clinical findings can be retrieved. However, the definition of clinical findings cannot cover all clinical findings, and therefore the retrieval of clinical findings may skip important information. This patent does note cope with the problem of false positive results, where too many non-relevant results are being retrieved.

Medical search needs to differentiate between findings and no findings—e.g. the difference between the following cases:
- there is no parenchymal nodule or pleural effusion
- no evidence of parenchymal lesions
- there are parenchymal changes
- Post-Radiation Changes of the Lung Parenchyma Doctors and researches need to be able to ask to exclude all cases with no pathological finding, otherwise the system becomes unusable. It is of paramount importance to identify no finding of pathological concepts and tag it as no finding so they can be excluded from the result set, if the user request so. Hence, there is a requirement for a search method that will assure reliable and comprehensive information retrieval.

SUMMARY OF THE INVENTION

The information retrieval method described in this invention is comprised of two phases. It is designed to retrieve information from a corpus, which contains huge number of documents. In the first phase each new document, which is added to the corpus, goes through tagging process. In this process, tags are added to sentences in the document according to the content of the sentence. The Tags are defined in a Tag Definition Table, where each tag can have plurality of description phrases called tag descriptors. When the content of a sentence is similar to a tag's descriptor, then the Tag is added to the sentence in the incoming document. The Tags define the opposite (negative) result of an expected query. Thus, if an expected query looks for high fever, then the Tag's descriptor defines cases of not high temperature (i.e. low temperature).

The Tag Definition Table (TDT) is defined by experts in the relevant field. For medical records, the TDT is prepared by doctors. The TDT is updated by the experts whenever a new definition is required.

In the next phase, a query is being processed. The query intends to find all cases of a pathological finding. The query processing phase involves two steps. In the first step all occurrences of the pathological subject are retrieved. The outcome of this step is an Initial Result List that contains documents with pathological findings and documents which does not contain pathological finding. In the next step, those documents that do not include pathological findings are filtered out from the Result List. Thus, only relevant documents, i.e. those which contain pathological findings remain in the Result List.

For example if the query intends to find pathological observations in the lungs, it first retrieves all documents which contains reference to the lungs the Initial Result Set. However, this Initial result set will include a document in which the following sentence may appear: "There are also no hyper metabolic foci suggestive of metastatic lesions including in lungs". This is a false positive case since the it does not contain pathological finding in the lungs. This document has to be filtered out from the Initial Result List. This sentence will be filtered out because it was tagged as No-Finding in the first phase of the document processing.

It is an objective of the disclosed invention to minimize the false positive and false negative results of the query, i.e. minimize the retrieval of non-relevant results as well as minimizing exclusion of relevant results.

It is also an object of the disclosed invention to work efficiently when huge number of documents are stored in the corpus.

In order to make sure that the Tag is properly defined, it can be updated by the user according to the result of the query.

BRIEF DESCRIPTION OF THE DRAWINGS

FIG. 2 presents a flow chart of an embodiment of the processing of the query.

DETAILED DESCRIPTION

The invention will be described more fully hereinafter, with reference to the accompanying drawings, in which a preferred embodiment of the invention is shown. The invention may, however, be embodied in many different forms and should not be construed as limited to the embodiment set forth herein; rather this embodiment is provided so that the disclosure will be thorough and complete, and will fully convey the scope of the invention to those skilled in the art.

Before describing the processing that each word goes through, it is important to explain the corpus of the system. The corpus of the system is a database that stores information on each document, sentence and each word ever entered the system, documents that constitute the search domain. Among the information on each sentence and word, the system corpus keeps a list of all words and their locations within the document as well as the sentence number within the document where that word is located, referred to as the search indexes. It also contains a phonetic representation for each word as well as statistical information on the word. Also it contain a dictionary of semantic synonyms of each word, including cross language synonyms. The result is that a search phrase entered by the user is transformed into multiple phrases that express the original in different ways—called Derived Queries.

The no finding queries work the same but the tag is of type "no finding" which is used by the system as signal to filter it out when the user request only positive findings.

The system maintains a table, which defines No-Finding Tag definitions. An example of such a table is shown in Table 1. Each line in the table defines the TAG and its descriptors. The descriptor is a phrase. A TAG may have more than one descriptor. When a sentence in a document contains similar information to that of a TAG's descriptor, the TAG is added to No Finding Tagged Document Table, an example of which is shown in table 2.

TABLE 1

No-Finding Tag Definition Table

| NO-FINDING TAG | NO-FINDING TAG'S DESCRIPTOR |
|---|---|
| Lung <NF> | Lungs free of active disease |
| | no hyper metabolic foci suggestive of metastatic lesions in lungs |
| Spleen <NF> | No significant abnormality of the spleen |
| | There is uniform activity in the spleen |
| Adrenals <NF> | No findings suggestive of metastatic disease activity in adrenals |
| | Low temperature |
| General no finding <NF> | There are no additional significant findings |
| | normal |

TABLE 2

No-Finding Tagged Document-Sentence Table

| DOCUMENT ID. | TAG | SENTENCE ID. | MATCHING SCORE |
|---|---|---|---|
| 12345 | <NF> spleen | 5 | 0.8 |
| | lung> <NF> | 18 | 0.92 |

Figure 1:
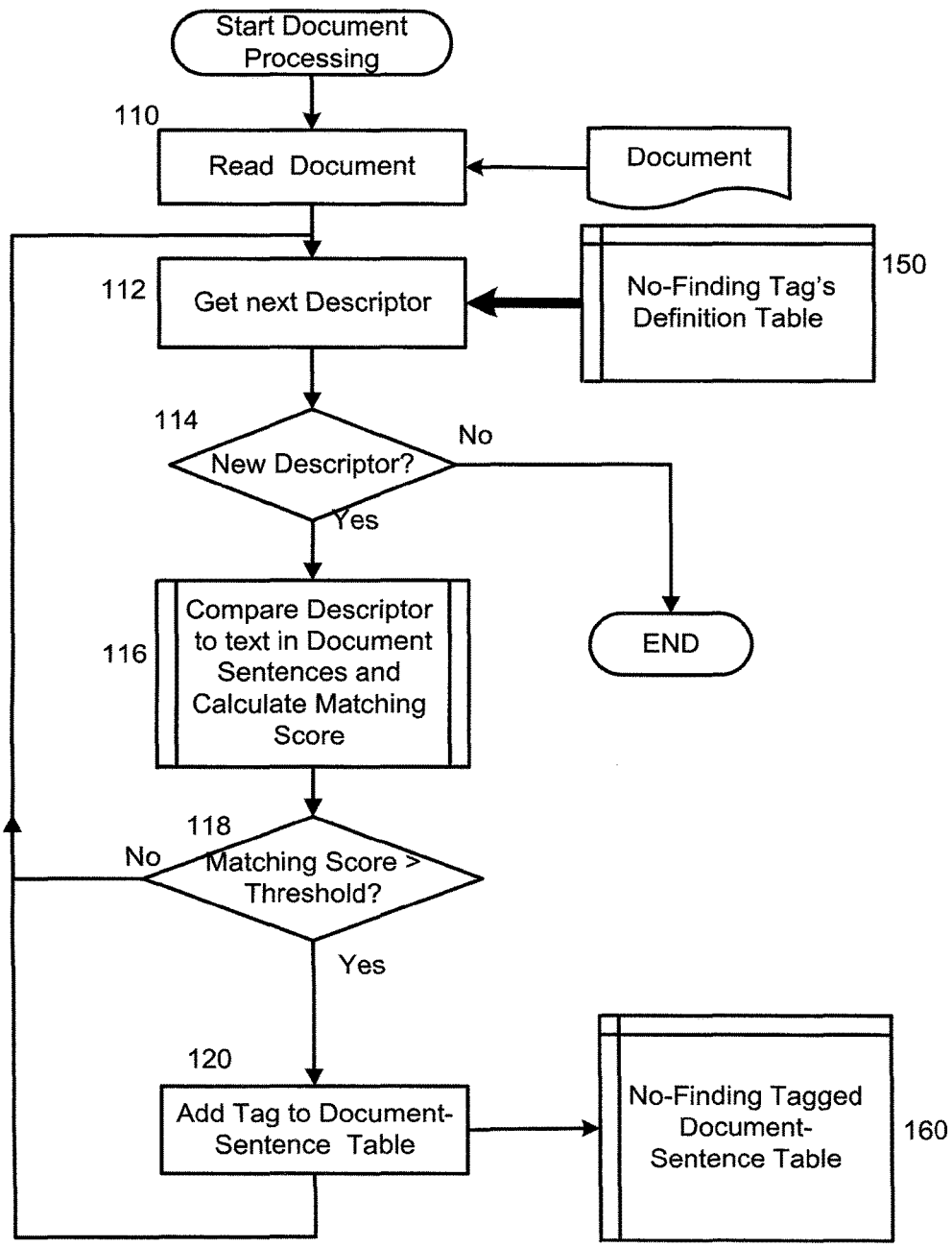
FIG. 1 presents a flow chart of the search preparation process.

The flow chart of one embodiment of the preparation process is shown in FIG. 1. Each new medical document, which is part of the search domain, goes through the preparation process. After reading the new document in step 110, it goes through the loop of steps 112 to 120, where each sentence of the document is compared to TAG's descriptor, and when match is found, the TAG is added to the No-Finding Tagged Document-Sentence Table. In step 112, a new descriptor is fetched from the list of No-Finding Tag's Definition Table—150. If all descriptors were processed, as tested in step 114, then the processing of the document terminates. Otherwise, the new fetched descriptor is compared to the sentences in the document and a matching score is predefined threshold, than step 120 is executed where the Tag of the matching descriptor is added to the No-Finding Tagged Document-Sentence table 160.

One embodiment of the processing of a query is shown in FIG. 2. The user enters a search request. The search request is a word or phrase expressing a finding. For example, the user wants to find all cases with pulmonary edema. Using ontology 250, comprehensive set of search expressions is generated. A document from the corpus is retrieved—in step 214 and is searched in step 216 to find matching phrases to the set of search expressions. A score is assigned to every match. Only those matches whose score is higher than a predetermined threshold are considered phrase detection. If the desired phrase was detected, as tested in step 218, then the system checks if the retrieved sentence in the document was tagged—with "no finding" tag step 220. If the sentence was not tagged with "no finding" tag, it is assumed that it did not contain no-finding, and the document is added, in step 222 to the result list 270. If the retrieved sentence was tagged with "no finding" tag, then this sentence in step 224, is added to the Removed Result List 280.

Figure 2A:
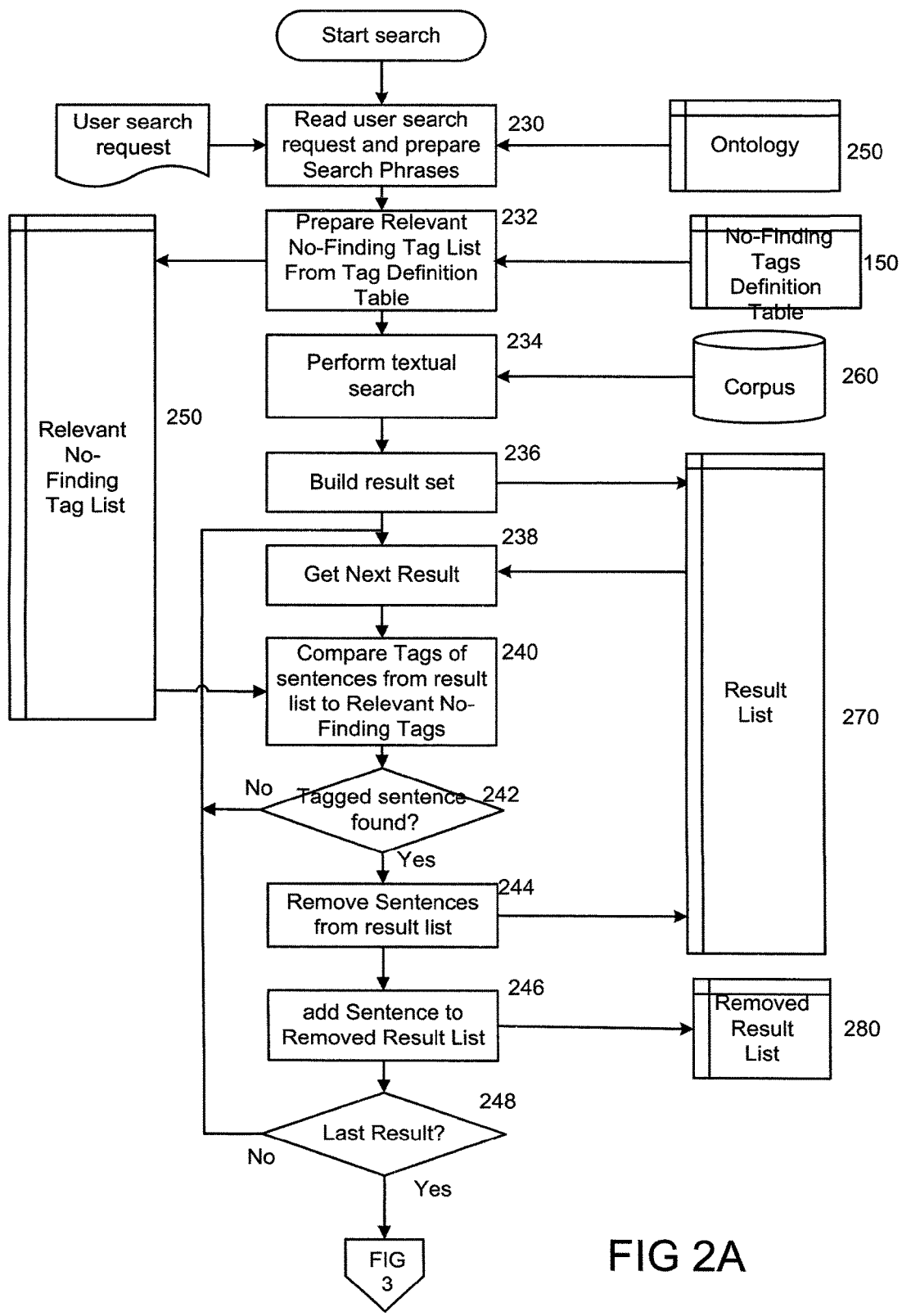
FIG. 2A presents a flow chart of another embodiment of the processing of the query.

If there is no sentence in the document that contain the search phrase and is not tagged with "no finding" tag, then the document is removed from the list Another implementation of the processing of the query is shown in FIG. 2A. The user enters the search request in order to find documents that contains a finding. For example, the user wants to find cases with findings in the lungs, so he enters the word "lung". The system receives the user request, and using ontology 250, prepares Search List—step 230. The system then, in step 232, extracts from the List of No-Finding Tags Definition table 150, relevant No-Finding Tags and saves it in a list —250 called Relevant-No-Finding Tag List. The system proceeds to step 234 in which the corpus is searched for all sentences that contain the search phrases, and in step 236, the initial Result List —270—is generated.

Each result in the Result List goes through loop consisting of steps 238 to 248. In step 238, a result from the Result List is fetched. In step 240 the Tags of the sentences from the Result List 270, are compared to the Tags in the Relevant No-Finding Tag list 250. If match is found—step 242—Then step 244 is executed where the sentence with the matched Tag is removed from the Result List 270, followed by step 246 where a Removed Result List 280 is updated. In step 242, if tagged sentence from the Result List 270 is not found in the Relevant No-Finding Tag 250, then next sentence is processed. In step 248, if not all sentences in the Result List 270 have been processed then the next sentence is fetched and processed.

Figure 3:
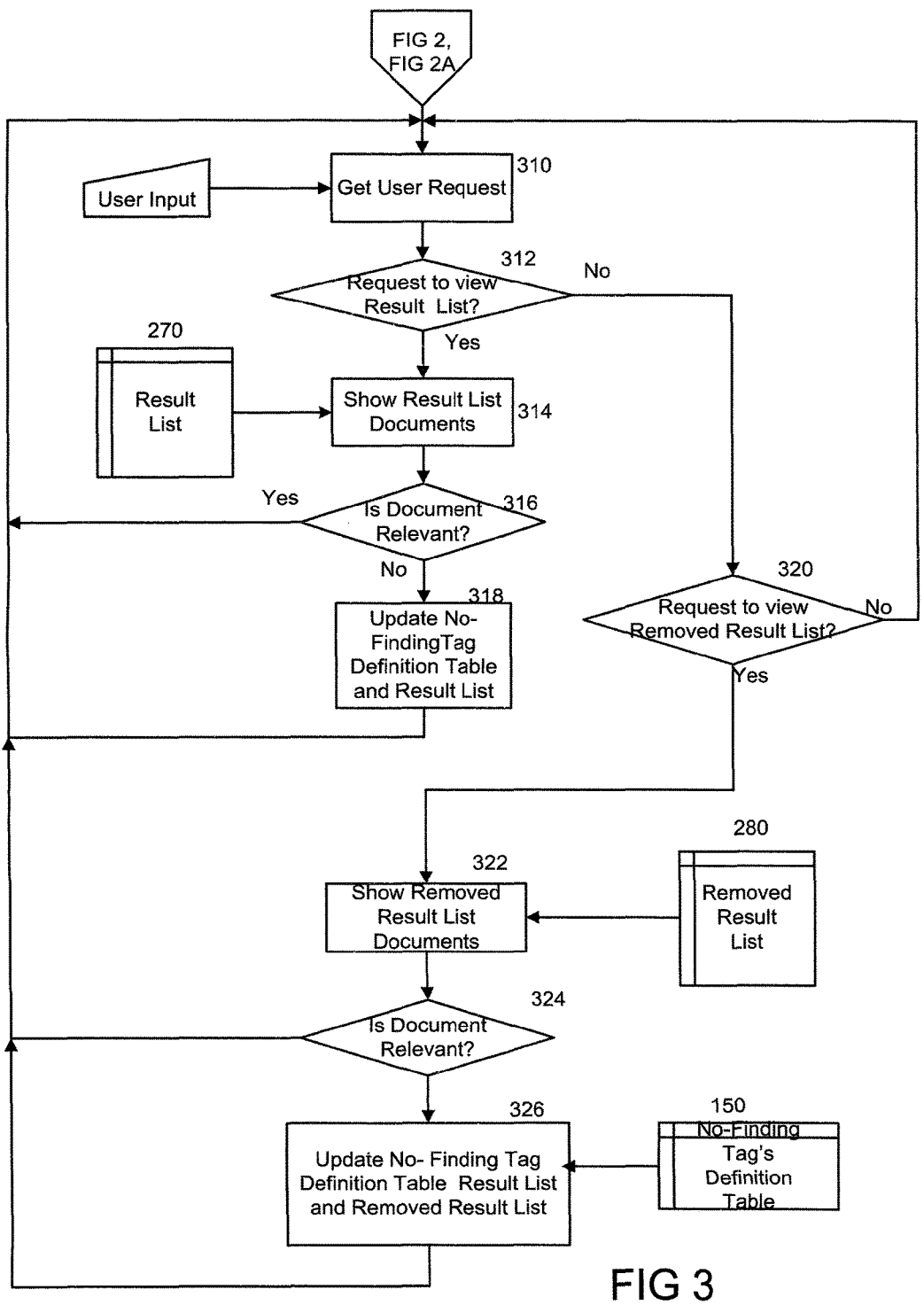
FIG. 3 presents a flow chart of search refinement phase.

The user can see both the Result List and the Removed Result List, as shown in FIG. 3. If he finds that the Result List contains a document that should not have been included in the Result List, it means that It was not removed. The user can update the Tag Definition Table so that this document will be tagged with No-Finding Tag, so next time it will be automatically removed from the Result List. The user request is received in step 310. If the request is to view the Result List as tested in step 312, then the Result List is shown—step 314. The user can view the content of any document in the Result List. If the user finds that a document in the Result List is not relevant—step 316, then he can, if he so wishes Update the Result List and/or Update the Tag Definition Table—step 318. The document can be removed from the Result List. The Tag Definition Table can be updated by addition of a new Tag Descriptor.

If the user requests to view the Removed Result List—step 320, then the list is presented to the user who can open and view any document in the list —322. If the user finds that a document is relevant—step 324, i.e. it should have been included in the Result List, he can add the document to the Result List and remove it from the Removed Result List—step 326. The user can also update the No-Finding Tag Definition Table by deleting the Tag Descriptor that erroneously caused the tagging of the document.

What is claimed is:

1. A method for performing search to retrieve pathological findings from medical report documents stored in a corpus, the method is comprised of the following steps:
   a. tagging sentences in the corpus documents according to the definition in the No-Finding Tag Definition Table, where plurality of sentences may be tagged in the same document;
   b. receiving a query regarding the search subject from the user;
   c. preparing No-Finding Tag List from the tag descriptors in Tag Definition Table which are relevant to the search subject;
   d. preparing a list of all documents in the corpus which contains at least one tag from the No-Finding Tag List, generating Removed Result List;
   e. searching the documents in the corpus for preparing a Result List containing all documents related to the search subject;
   f. removing from the Result List all documents in the Removed Result List; and
   g. presenting the Result List and the Removed Result List to the user.

2. The method according to claim 1 wherein the definition in the No-Finding Tag Definition Table constitutes a query applied to the documents in the corpus.

3. The method according to claim 1 wherein a query generated by the user or derived from the No-Finding Tag Definition Table, using the dictionary of semantic synonyms, is transferred into multiple phrases that express the original query called derived queries.

4. The method according to claim 3 wherein the Removed Result List is derived by comparing the match level between the derived queries from the No-Finding Tag Definition Table and the sentences in the documents.

5. The method according to claim 1 wherein the user can modify the Tag Definition Table.

6. The method according to claim 4 wherein the relevant no-finding tags are derived by comparing the match level between derived queries from the No-Finding Tag Definition Table and the derived queries from the user generated query.

7. A computer system comprising one or more computers configured to perform operations for retrieving pathological findings from medical reports stored in a corpus, operations comprising the steps of:
   a. tagging sentences in the corpus documents according to the definition in the No-Finding Tag Definition Table, where plurality of sentences may be tagged in the same document;
   b. receiving a query regarding the search subject from the user;
   c. preparing No-Finding Tag List from the tag descriptors in Tag Definition Table which are relevant to the search subject;
   d. preparing a list of all documents in the corpus which contains at least one tag from the No-Finding Tag List, generating Removed Result List;
   e. searching the documents in the corpus for preparing a Result List containing all documents related to the search subject preparing a Result List containing all documents related to the search subject;
   f. removing from the Result List all documents in the Removed Result List; and
   g. presenting the Result List and the Removed Result List to the user.

8. A computer system according to claim 7, further including steps to generate multiple search phrases based on a query, using dictionary of semantic synonyms.

\* \* \* \* \*